United States Patent
Alruhaimi

(10) Patent No.: US 10,357,341 B2
(45) Date of Patent: Jul. 23, 2019

(54) BONY BRACKET SCREW

(71) Applicant: KING SAUD UNIVERSITY, Riyadh (SA)

(72) Inventor: Khalid Abdullah Ibrahim Alruhaimi, Riyadh (SA)

(73) Assignee: King Saud University, Riyadh (SA)

( * ) Notice: Subject to any disclaimer, the term of this patent is extended or adjusted under 35 U.S.C. 154(b) by 24 days.

(21) Appl. No.: 15/355,046

(22) Filed: Nov. 17, 2016

(65) Prior Publication Data

US 2018/0132978 A1   May 17, 2018

(51) Int. Cl.
*A61C 8/00* (2006.01)
*A61C 7/28* (2006.01)
*A61C 7/10* (2006.01)

(52) U.S. Cl.
CPC .............. *A61C 8/0096* (2013.01); *A61C 7/10* (2013.01); *A61C 7/282* (2013.01); *A61C 8/0012* (2013.01); *A61C 8/0024* (2013.01); *A61C 8/0048* (2013.01)

(58) Field of Classification Search
CPC ........... A61C 8/0096; A61C 8/00; A61C 7/28; A61B 17/8605; A61B 17/861; A61B 17/8615; A61B 17/862
USPC .............................................. 433/18; 606/305
See application file for complete search history.

(56) References Cited

U.S. PATENT DOCUMENTS

| | | | |
|---|---|---|---|
| 5,921,774 A * | 7/1999 | Kanomi | A61C 7/00 433/173 |
| 6,592,366 B2 | 7/2003 | Triaca et al. | |
| 7,934,927 B2 * | 5/2011 | Yazdi | A61C 7/00 433/18 |
| 2002/0018978 A1 * | 2/2002 | Triaca | A61B 17/663 433/7 |
| 2002/0127510 A1 * | 9/2002 | Kyung | A61C 8/00 433/18 |
| 2004/0157187 A1 * | 8/2004 | Lin | A61C 7/00 433/18 |
| 2005/0084822 A1 | 4/2005 | Stucki-McCormick | |
| 2005/0095550 A1 * | 5/2005 | Kim | A61C 8/0022 433/18 |

(Continued)

FOREIGN PATENT DOCUMENTS

| CN | 85202741 U | 12/1986 |
|---|---|---|
| DE | 202005017462 U1 | 4/2006 |

OTHER PUBLICATIONS

"Suspend-It 8857 Eye Lag Screw," http://www.walmart.com/ip/SUSPEND-IT-8857-Eye-Lag-Screw-1-4-Thread-For-Metal-Pk-50/40743027 (Last Accessed on May 16, 2016) 2pgs.

*Primary Examiner* — Si Ming Ku
(74) *Attorney, Agent, or Firm* — Richard C. Litman

(57) ABSTRACT

The bony bracket screw has a cross-slot head or a Phillips head and a shank extending from the head, the shank having a smooth upper portion, a threaded lower portion, and a self-tapping or self-drilling tip. The screw has an annual flange defining a stop disposed between the smooth upper shank and the threaded lower shank. The stop may have a larger diameter than the head. The screw has a bracket arm extending from the smooth upper shank at an oblique angle. The free end of the bracket arm has a round retainer, which may be circular or cylindrical and defines a smooth bore adapted for supporting a distractor or other dental appliance. The screw may be made from stainless steel or other noncorrosive, biocompatible material.

6 Claims, 4 Drawing Sheets

(56) References Cited

U.S. PATENT DOCUMENTS

2010/0160920 A1  6/2010  Mommaerts
2015/0250567 A1  9/2015  Buddemeyer et al.

* cited by examiner

BONY BRACKET SCREW

BACKGROUND OF THE INVENTION

1. Field of the Invention

The present invention relates to surgical screws and fasteners used in dentistry and maxillofacial orthopedics, and particularly to a bony bracket screw that has a bracket arm extending at an oblique angle to the shaft or shank of the screw for supporting a distractor or other maxillofacial fixing and dental appliance.

2. Description of the Related Art

Distraction osteogenesis is a process of lengthening bone in a gradual manner by distracting or separating one surgically sectioned bony part from an adjacent surgically sectioned bony part under traction with the use of a distractor device while the growth of new bone tissue rejoins the separated bones. The distraction is typically performed in small daily increments, and generally results in the formation of new bone between the separated bony parts. The procedure is used to lengthen short bones or generate new bone in a defective or deficient bony site without the need for a bone graft.

Distraction devices typically require a strong holding plate bracket to grip the traction bar. The use of a strong holding plate bracket, however, requires the creation of a surgical flap. The creation of a surgical flap not only prolongs the time in which the patient spends in surgery, but it also lengthens the time necessary for recovery. A tooth band bracket also typically cannot be used in cases where the selected teeth are too weak to hold the band bracket or when the investing bone level around the roots of the teeth is short or periodontally involved with reabsorbed bone around the roots of the selected teeth and not strong enough to withstand the forces of distraction and the anchor load exerted by the traction forces. Further, at times the stability of the tooth band bracket against the attraction forces of the moving bony segment may be a cause for concern.

Thus, a bony bracket screw solving the aforementioned problems is desired.

SUMMARY OF THE INVENTION

The bony bracket screw has a cross-slot head or a Phillips head and a shank extending from the head, the shank having a smooth upper portion, a threaded lower portion, and a self-tapping or self-drilling tip. The screw has an annual flange defining a stop disposed between the smooth upper shank and the threaded lower shank. The stop may have a larger diameter than the head. The screw has a bracket arm extending from the smooth upper shank at an oblique angle. The free end of the bracket arm has a round retainer, which may be circular or cylindrical and defines a smooth bore adapted for supporting a distractor or other dental appliance. The screw may be made from stainless steel or other noncorrosive, biocompatible material.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The bony bracket screw has a cross-slot head or a Phillips head and a shank extending from the head, the shank having a smooth upper portion, a threaded lower portion, and a self-tapping or self-drilling tip. The screw has an annual flange defining a stop disposed between the smooth upper shank and the threaded lower shank. The stop may have a larger diameter than the head. The screw has a bracket arm extending from the smooth upper shank at an oblique angle. The free end of the bracket arm has a round retainer, which may be circular or cylindrical and defines a smooth bore adapted for supporting a distractor or other dental appliance. The screw may be made from stainless steel or other noncorrosive, biocompatible material.

Figure 1:
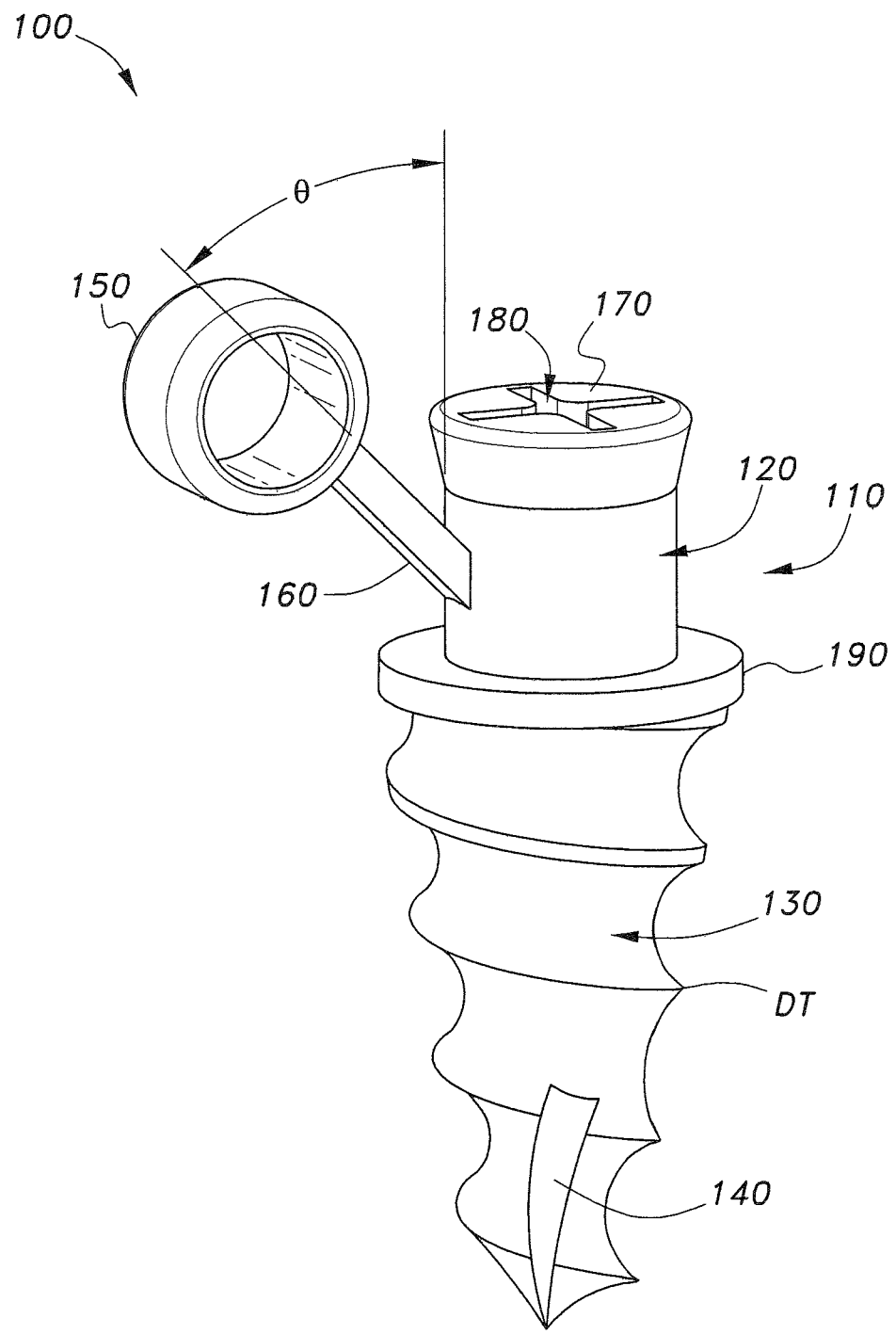
FIG. 1 is a perspective view of a bony bracket screw according to the present invention as seen from a side of the screw.
Figure 2:
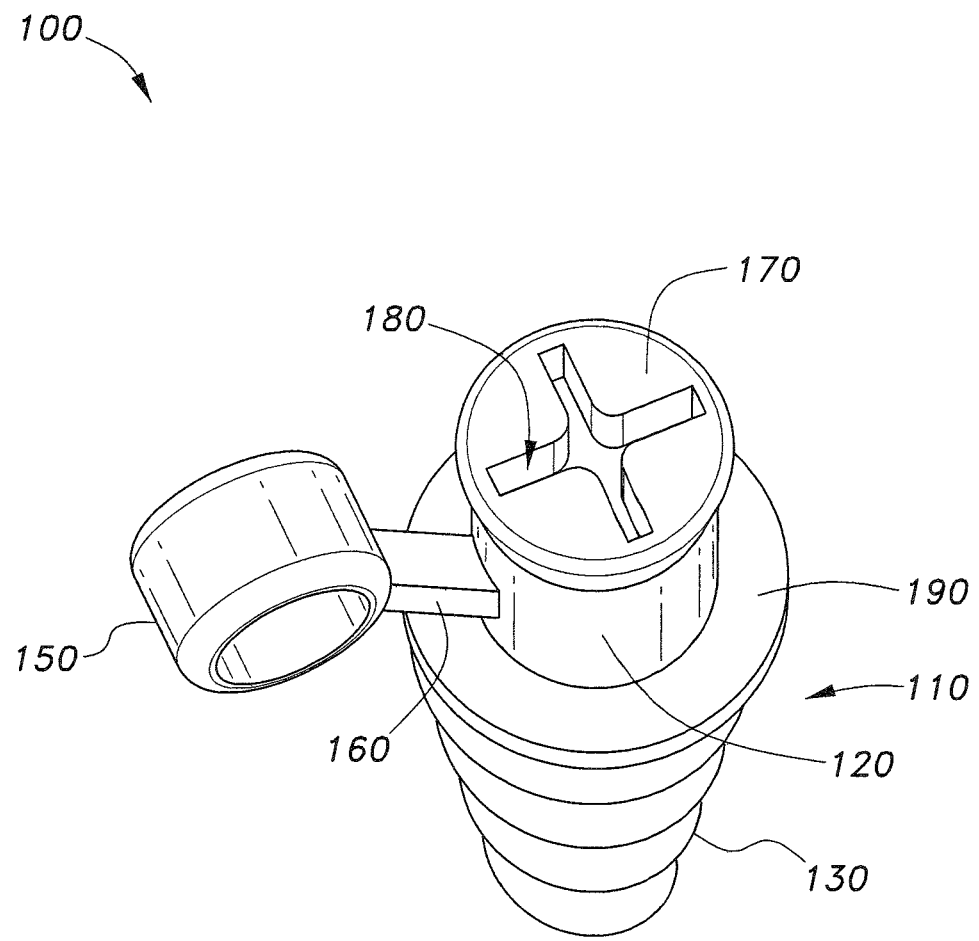
FIG. 2 is a perspective view of the bony bracket screw of FIG. 1 as seen from the top of the screw.

As shown in FIGS. 1-2, the bony bracket screw 100 has a head 170 and a shank 110 extending from the head 170. The head 170 has a cruciform slot 180 defined therein. The cruciform slot 180 may be a crossed-slot head or a Phillips head. As used herein, the term "crossed-slot" head refers to two slots of substantially uniform depth that extend across substantially the entire diameter of the head 170. The crossed-slot head is designed to be used with a flat blade driver, which may alternately be inserted into one slot or the other to drive the screw, depending upon the presentation or accessibility of the head. Alternatively, the cruciform slot may be the well-known recessed cruciform slot known as a Phillips head, designed for use with a Phillips driver, which will slip from the cruciform slot 180 when the screw has been sufficiently fastened in order to avoid over-torqueing the screw 100.

The shank 110 has a smooth upper portion 120 and a threaded lower portion 130. the threaded lower portion being defined by a tapering inclined plane DT helically extending down the lower portion 130 of the shank 110 in conventional pattern. The lower portion 130 of the shank 110 terminates in a self-tapping or self-drilling tip 140 formed by a slot extending through the bottom two rotations of the helical thread DT, defining cutting edges. An annular flange 190 defined a stop disposed between the smooth upper portion 120 and threaded lower portion 130 of the shank 110. As best seen in FIG. 2, the stop 190 may have a greater diameter than the head 170. The stop 190 prevents the screw 100 from passing too deeply through the mucoperiosteum when fixing the screw to the bone.

Figure 3:
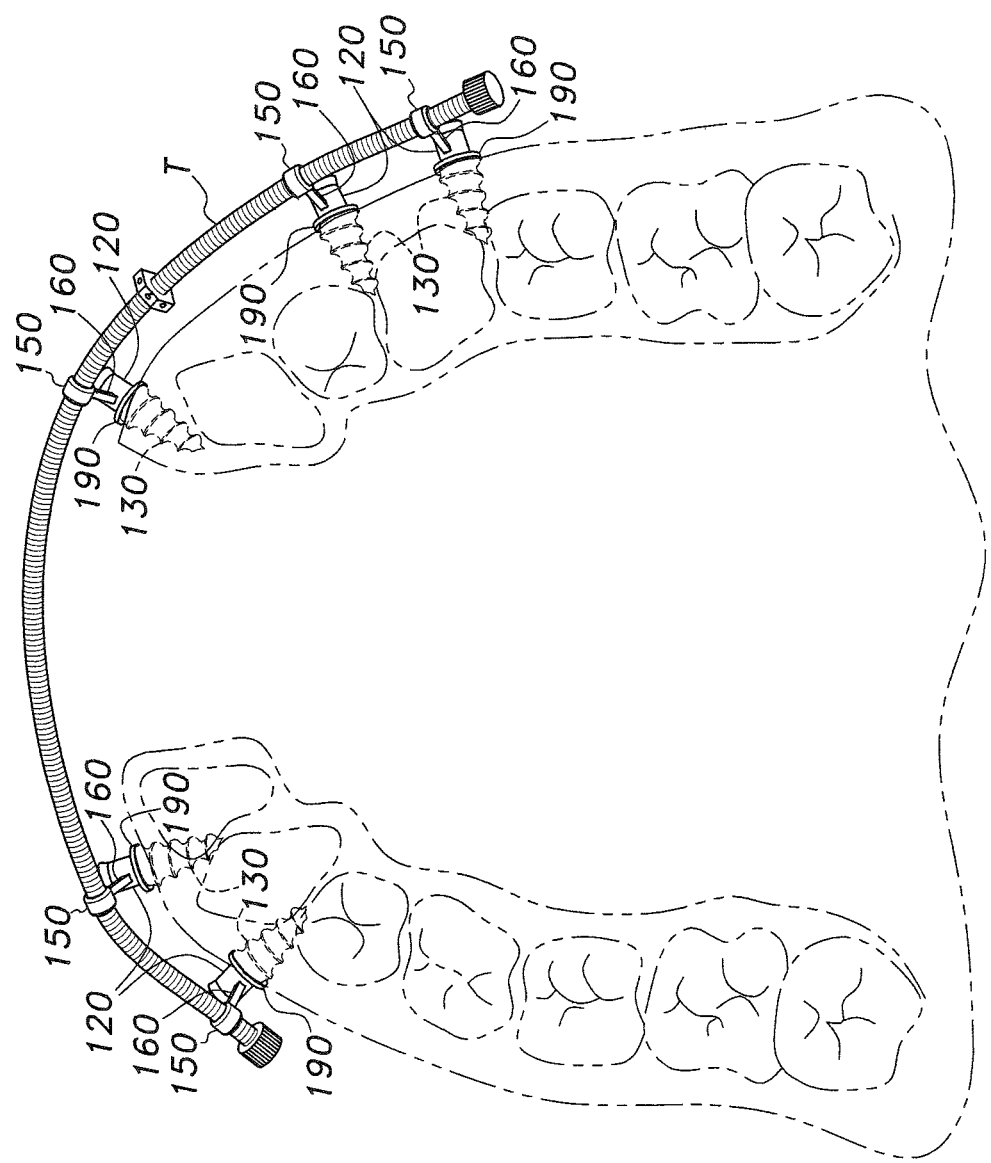
FIG. 3 is an environmental top view of an anterior curved distractor secured to the maxilla or upper jaw of a person's mouth by a plurality of the bony bracket screws of FIG. 1.
Figure 4:
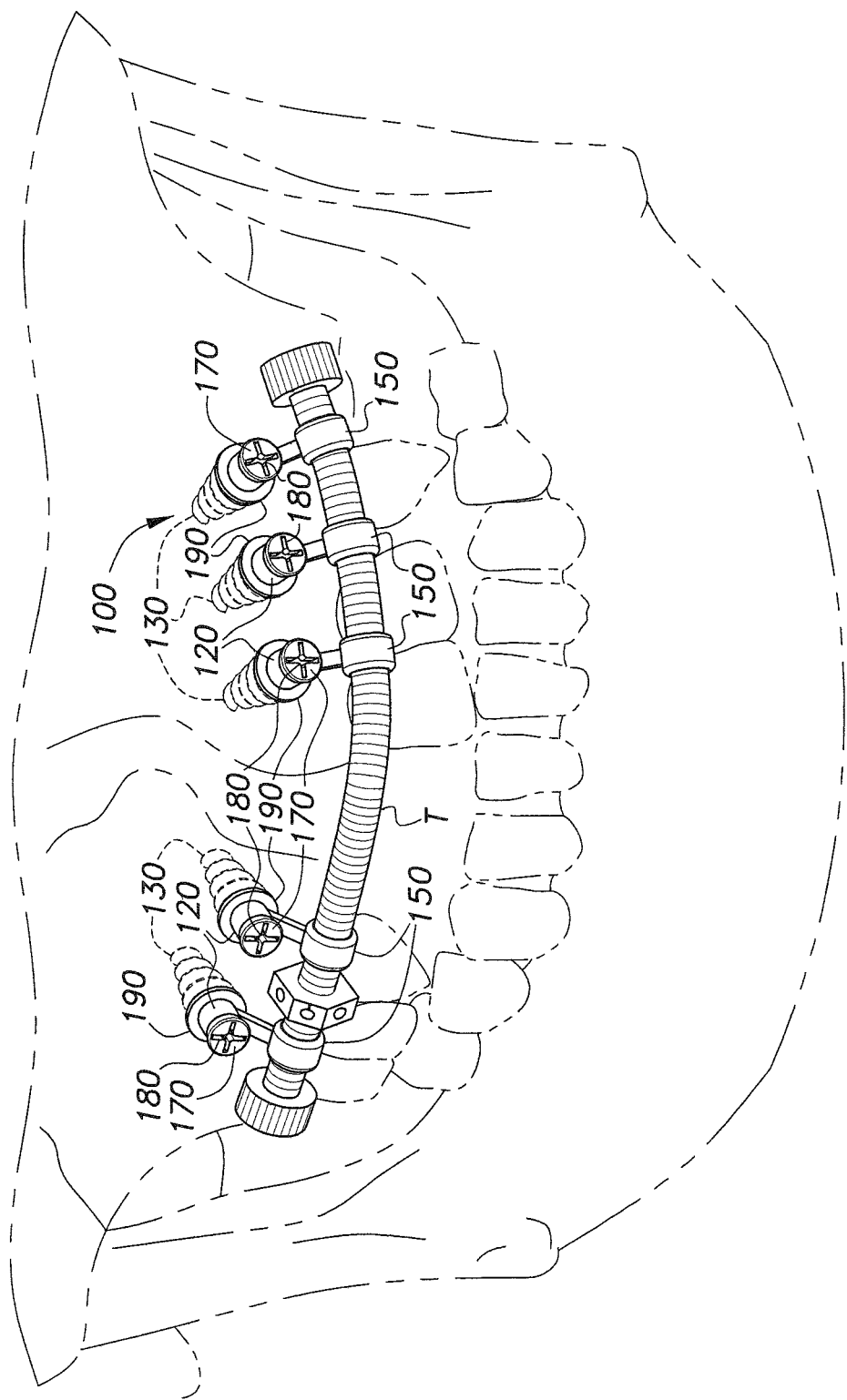
FIG. 4 is an environmental front view of an anterior curved distractor secured to the upper jaw of a person's mouth by a plurality of the bony bracket screws of FIG. 1.

A bracket arm 160 extends from the smooth upper portion 120 of the shank 110 at an oblique angle θ. The oblique angle θ may be, e.g., about 45° (or 135°, depending upon whether the angle is measured with respect to the ascending portion of the axis of the shank 110 or the descending portion), although oblique angles θ greater or less 45° may be used, depending upon the application. The bracket arm 160 terminates in a circular or cylindrical retainer 150 that has a smooth bore for supporting a traction bar T or other appliance, as shown in FIGS. 3 and 4. FIGS. 3 and 4 are environmental views showing a representative use of a plurality of the bony bracket screws 100 to support the traction bar T of an anterior curved distraction device.

Representative dimensions of the bony bracket screw 100 include a length of at least 12 mm and a thickness of about 2 mm. The length of the threaded lower portion 130 of the shank 110 may be at least 6 mm. The bracket arm 160 may be provided in different lengths to offset the retainer 150 at different distances or heights, depending on the application. Representative lengths of the bracket arm 160 include a length approaching 0 mm, 2 mm, or 4 mm. The retainer 150 may have an outer diameter of about 4 mm and a thickness of about 2 mm, defining a bore having an inner diameter of 2 mm. The stop 190 may have a diameter of 4 mm and a thickness of 1 mm. The threads of the threaded lower portion 130 of the shank 110 may have a pitch of 1 mm. It will be understood that the recitation of dimensions herein is provided for purposes of enablement, and not by way of limitation. Actual dimensions are a manufacturing detail, and may vary from the dimensions recited herein.

It is to be noted that the bony bracket screw 100 can be used in conjunction with not only the traction bar T, but also with any type of distractor device, maxillofacial fixing device, or other type of dental appliance, such as for augmentation of defects resulting from cleft palate deformities, anterior congenital defects of the maxilla and the mandible, anterior jaw defects resulting from surgical removal of a cyst of pathogeneses and tumors, acquired anterior discontinuity of the maxilla or mandible defects, as well as defects due to trauma. The screws 100 may be fixed to the bone under local anesthesia, and provide a strong support for distraction devices and other dental appliances that can be installed and removed more quickly and easily than existing devices.

It is to be understood that the present invention is not limited to the embodiments described above, but encompasses any and all embodiments within the scope of the following claims.

I claim:

1. In combination, a distraction osteogenesis bar and a plurality of elongated bracket screws therefore, comprising:
   the distraction osteogenesis bar, wherein the distraction osteogenesis bar is configured and dimensioned for maxillofacial fixing;
   each of the plurality of elongated bracket screws consisting of:
   a head;
   a shank extending from the head, the shank having an upper portion, a threaded lower portion adjacent to the upper potion thereby defining a junction, and a self-tapping tip extending from the lower portion, wherein the head and the shank define a longitudinal axis;
   an annular flange disposed at the junction between the upper portion and the threaded lower portion of the shank thereby being contiguous to each of the upper portion and the threaded lower portion, the annular flange having a peripheral surface and a diameter greater than each of the head and the upper portion thereby forming a stop between the upper portion and the threaded lower portion;
   a bracket arm, the bracket arm having one end extending directly from the upper portion at an acute angle to the longitudinal axis, the bracket arm being adapted for supporting the distraction osteogenesis bar at the other end;
   a retainer at the other end of the bracket arm, the retainer defining a bore adapted for supporting the distraction osteogenesis bar therein, the bore having a longitudinal axis, wherein the retainer extends beyond the peripheral surface of the annular flange, further wherein the longitudinal axis of the bore extends perpendicular to the longitudinal axis of the head and shank; and
   wherein the distraction osteogenesis bar extends through each of the bores of each of the retainers.

2. The combination according to claim 1, wherein said head has cruciform slots defined therein.

3. The combination according to claim 1, wherein said head is a crossed-slot head.

4. The combination according to claim 1, wherein said head is a Phillips head.

5. The combination according to claim 1, wherein each of said elongated bracket screws is made from a noncorrosive, biocompatible material.

6. The combination according to claim 5, wherein said noncorrosive, biocompatible material is stainless steel.

* * * * *